(12) United States Patent
Apelstedt et al.

(10) Patent No.: US 12,357,498 B2
(45) Date of Patent: Jul. 15, 2025

(54) LID

(71) Applicant: OstomyCure AS, Oslo (NO)

(72) Inventors: Kristoffer Jens Olle Apelstedt, Jönköping (SE); David Karl Theodor Hvirf, Jönköping (SE); Sandra Ida Maria Carling, Jönköping (SE); Mats Erik Kindahl Cardell, Nacka (SE)

(73) Assignee: OstomyCure AS, Oslo (NO)

( * ) Notice: Subject to any disclaimer, the term of this patent is extended or adjusted under 35 U.S.C. 154(b) by 0 days.

(21) Appl. No.: 18/858,404

(22) PCT Filed: Apr. 24, 2023

(86) PCT No.: PCT/EP2023/060651
§ 371 (c)(1),
(2) Date: Oct. 21, 2024

(87) PCT Pub. No.: WO2023/203250
PCT Pub. Date: Oct. 26, 2023

(65) Prior Publication Data
US 2025/0169981 A1  May 29, 2025

(30) Foreign Application Priority Data
Apr. 22, 2022 (EP) .................... 22169487

(51) Int. Cl.
*A61F 5/445* (2006.01)
*A61F 5/44* (2006.01)
(Continued)

(52) U.S. Cl.
CPC ...... *A61F 5/445* (2013.01); *A61F 2005/4486* (2013.01)

(58) Field of Classification Search
CPC ... A61F 5/445; A61F 2005/4486; A61F 5/443
See application file for complete search history.

(56) References Cited

U.S. PATENT DOCUMENTS 4,381,765 A * 5/1983 Burton .................... A61F 5/445
604/277
4,634,421 A * 1/1987 Hegemann ............ A61F 2/0009
604/277
(Continued)

FOREIGN PATENT DOCUMENTS

EP      3181101 A1    6/2017
GB       810517 A     3/1959
(Continued)

OTHER PUBLICATIONS

International Search Report & Written Opinion dated Jun. 7, 2023 pertaining to PCT International application No. PCT/EP2023/060651 filed Apr. 24, 2023, pp. 1-13.

*Primary Examiner* — Guy K Townsend
(74) *Attorney, Agent, or Firm* — DINSMORE & SHOHL LLP

(57) ABSTRACT

The present disclosure relates to a lid for an ostomy implant, comprising: a ring-shaped base part adapted to engage with an open end of the ostomy implant; a cap part adapted to fit inside the ring-shaped base part, wherein the cap part is rotatable with respect to the ring-shaped base part to lock and unlock the lid to the ostomy implant, and wherein the cap part has a through-hole; and a slider configured to be radially slid into a recess of the cap part in a closed configuration, wherein the slider completely covers the through-hole of the cap part, and radially slid out from the recess in an open configuration, wherein the slider does not cover the through-hole of the cap part. The disclosure further relates to a method of manufacturing the lid.

20 Claims, 10 Drawing Sheets

(51) Int. Cl.
*A61F 5/443* (2006.01)
*A61F 5/448* (2006.01)

(56) References Cited

U.S. PATENT DOCUMENTS

| | | | | |
|---|---|---|---|---|
| 4,804,375 | A * | 2/1989 | Robertson | A61F 2/0013 604/323 |
| 4,863,438 | A * | 9/1989 | Gauderer | A61M 39/0247 604/105 |
| 6,033,390 | A * | 3/2000 | von Dyck | A61F 5/445 604/174 |
| 6,485,476 | B1 * | 11/2002 | von Dyck | A61F 5/441 604/332 |
| 6,595,971 | B1 * | 7/2003 | von Dyck | A61M 3/0202 604/334 |
| 7,087,041 | B2 * | 8/2006 | von Dyck | A61F 5/445 604/338 |
| 7,452,347 | B2 * | 11/2008 | DeLegge | A61J 15/0057 604/910 |
| 8,043,260 | B2 * | 10/2011 | DeLegge | A61M 39/12 604/910 |
| 8,192,410 | B2 * | 6/2012 | Smith | A61F 5/445 604/327 |
| 8,998,867 | B2 * | 4/2015 | Sabeti | A61F 5/4405 604/335 |
| 9,636,249 | B2 * | 5/2017 | Davies | A61F 5/445 |
| D818,590 | S * | 5/2018 | Cardell | D24/155 |
| 10,441,455 | B2 * | 10/2019 | Eggert | A61F 5/4405 |
| 11,395,757 | B2 * | 7/2022 | Eggert | A61F 5/445 |
| 2002/0077611 | A1 * | 6/2002 | von Dyck | A61F 5/442 604/332 |
| 2012/0245535 | A1 * | 9/2012 | Jacobsson | A61F 5/445 604/264 |
| 2013/0060213 | A1 * | 3/2013 | Hanuka | A61F 5/441 604/344 |
| 2013/0116636 | A1 | 5/2013 | Carrubba | |
| 2015/0094675 | A1 | 4/2015 | Kyvik et al. | |
| 2015/0141944 | A1 * | 5/2015 | Hanuka | A61F 5/442 604/338 |
| 2016/0030227 | A1 * | 2/2016 | Brönnimann | A61F 5/445 604/338 |
| 2016/0287428 | A1 * | 10/2016 | Eggert | A61F 5/445 |
| 2019/0175385 | A1 * | 6/2019 | Cardell | A61F 5/4407 |
| 2019/0224037 | A1 * | 7/2019 | Bell | A61F 5/4405 |
| 2019/0380860 | A1 * | 12/2019 | Eggert | A61F 5/4405 |
| 2021/0121317 | A1 * | 4/2021 | Brönnimann | A61F 5/449 |
| 2023/0277359 | A1 * | 9/2023 | Brönnimann | A61F 5/448 604/334 |

FOREIGN PATENT DOCUMENTS

| | | |
|---|---|---|
| WO | 2006046210 A1 | 5/2006 |
| WO | 2013014231 A1 | 1/2013 |
| WO | 2013168165 A2 | 11/2013 |
| WO | 2017216302 A2 | 12/2017 |
| WO | 2019197291 A1 | 10/2019 |

* cited by examiner

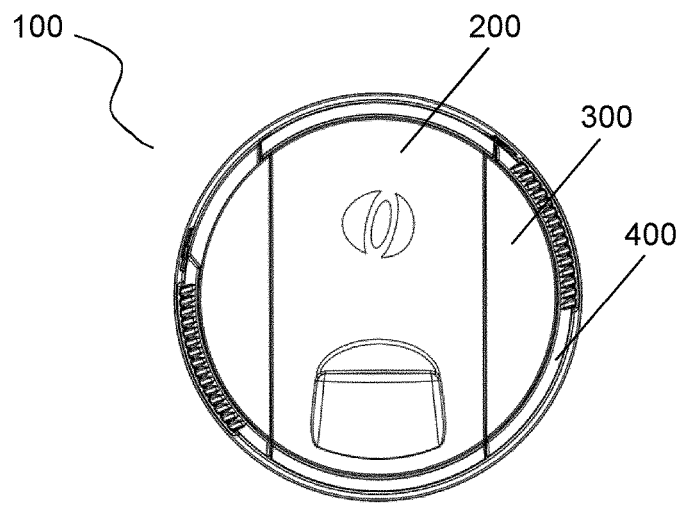
FIG. 15A
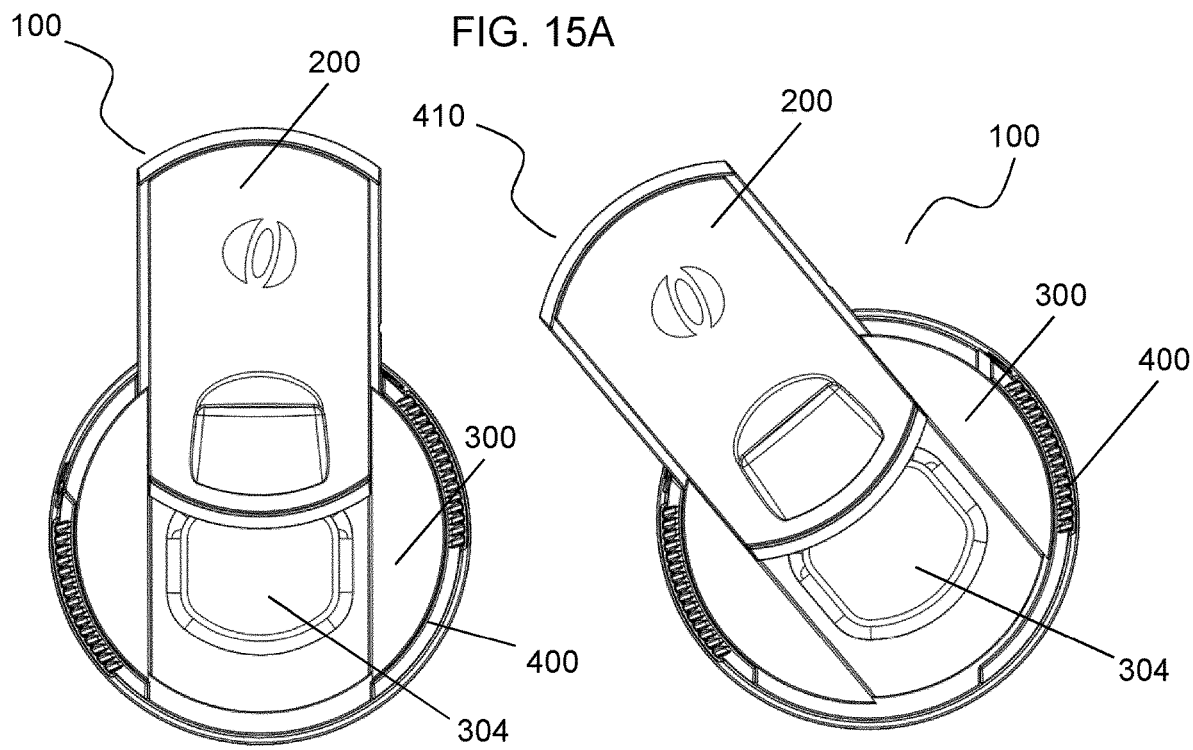
FIG. 15B
FIG. 15C

LID

CROSS-REFERENCE TO RELATED APPLICATIONS

The present application is the National Phase entry of International Patent Application No. PCT/EP2023/060651, filed Apr. 24, 2023, which claims priority to European Patent Application No. 22169487.0, filed Apr. 22, 2022, the entire contents of both are hereby incorporated by reference into this application.

TECHNICAL FIELD

The present disclosure relates to a lid. In particular, it relates to a lid for a medical implant, more particularly for an ostomy implant.

BACKGROUND

Ileostomy and colostomy are common operations which may be necessitated, for example, by malignancy or chronic bowel inflammation. The surgery is called an ileostomy if the colon and rectum are removed and a colostomy if the rectum alone is removed. Similarly, an abdominal urostomy is created when the urinary bladder has to be removed due to, for example, bladder cancer. In these operations, a stoma is formed in the abdominal wall to which a bowel segment is connected.

Ileostomy is a stoma constructed by bringing the end or loop of small intestine (the ileum) out onto the surface of the skin, or the surgical procedure which creates this opening. Intestinal waste passes out of the ileostomy and is collected in an external ostomy system which is placed next to the opening.

A colostomy is a stoma in the large intestine (colon), or the surgical procedure that creates one. The opening is formed by drawing the healthy end of the colon through an incision in the anterior abdominal wall and suturing it into place. This opening, often in conjunction with an attached ostomy system, provides an alternative channel for faeces to leave the body.

An ostomy pouching system is a medical device that provides a means for the collection of waste from a stoma. Traditional pouching systems usually consist of a collection pouch, a barrier on the skin, and connect with the stoma itself, which is the part of the body that has been diverted to the skin.

As an alternative to traditional ostomy pouching systems, an implant-based system has previously been developed. This system is based on a percutaneous ostomy implant, which is anchored in the body of the user and allows serosal tissue of a bowel segment to attach to the implant. The ostomy implant comprises a usually cylindrical body with an open end, to which a lid may be attached. When the lid is removed, the open end can be connected to an emptying device, such as an ostomy pouch. The solution allows the users to exercise their needs when it suits them and minimizes skin complications as well as discomfort, noise and smell.

However, the lids that are currently available for the ostomy implant-based solutions are associated with a number of inconveniences related to, for example, ease of use, robustness, manufacturing complexity etc.

The applicant's earlier international application WO 2017/216302 discloses one variant of a lid for an ostomy implant.

SUMMARY

The present disclosure relates to an improved lid for an ostomy implant, comprising:
- a ring-shaped base part adapted to engage with an open end of the ostomy implant;
- a cap part adapted to fit inside the ring-shaped base part, wherein the cap part is rotatable with respect to the ring-shaped base part to lock and unlock the lid to the ostomy implant, and wherein the cap part has a through-hole; and
- a slider configured to be radially slid into a recess of the cap part in a closed configuration, wherein the slider completely covers the through-hole of the cap part, and radially slid out from the recess in an open configuration, wherein the slider does not cover the through-hole of the cap part.

The ring-shaped base part is, preferably, configured to engage with a circumferential groove of the ostomy implant. By controlling the locking of the ring-shaped base part to the ostomy implant by means of rotation of the cap part, a solution that is easy to use for the wearer is obtained. In particular, the cap part may be rotated by holding and rotating the slider when the slider is in a retracted position.

The slider may thus have a double functionality in the lid assembly. Besides working as a handle for rotation of the cap to lock and unlock the lid to the ostomy implant, it may function as a retractable, liquid-tight cover of the through-hole of the cap part. In the closed configuration, which may also be referred to as an inserted position, the slider completely covers the through-hole of the cap part. In the open configuration, which may also be referred to as a retracted position, the slider does not cover the through-hole of the cap part. In this regard "does not cover" shall be interpreted as the slider not covering at least a part of the through-hole, which means that there is a fluid connection between the interior of the stoma and the exterior, which may be, for example, an ostomy pouch.

The cap part may comprise an upper gasket disposed around the through-hole. Preferably, the upper gasket is arranged in an upper cap groove and protrudes upwardly, towards the slider, from the recess of the cap part. Preferably, the upper gasket and the upwards protrusion of the same are dimensioned such that the slider can slide over it to reach the closed configuration, wherein the slider completely covers the through-hole of the cap part, but at the same time such that the slider and the upper gasket form a liquid-tight sealing in the closed configuration.

FIG. 1A-C show one embodiment of the presently disclosed lid comprising a ring-shaped base part (FIG. 1C), a cap part (FIG. 1B) and a slider (FIG. 1A). Preferably, the assembly does not have any loose parts, and is therefore perceived as one lid component by a user.

The ring-shaped base part may comprise a plurality of locking hooks configured to engage with a circumferential groove of the ostomy implant. The cap part may comprise a plurality of blocking elements that correspond to the plurality of locking hooks of the ring-shaped base part. Preferably, the plurality of blocking elements are configured to block the plurality of locking hooks to move from the circumferential groove of the ostomy implant when the lid is in a locked configuration.

The present disclosure further relates to a method of manufacturing the presently disclosed lid, the method comprising the steps of:
providing a ring-shaped base part adapted to engage with an open end of the ostomy implant;

providing a cap part adapted to fit inside the ring-shaped base part, wherein the cap part is rotatable with respect to the ring-shaped base part to lock and unlock the lid to the ostomy implant, and wherein the cap part has a through-hole;

providing a slider configured to be radially slid into a recess of the cap part in a closed configuration, wherein the slider completely covers the through-hole of the cap part, and radially slid out from the recess in an open configuration, wherein the slider does not cover the through-hole of the cap part; and assembling the ring-shaped base part, the cap part and the slider.

BRIEF DESCRIPTION OF THE DRAWINGS

FIG. 15 shows configurations of opening/closing and locking of the lid;

Figure 1A:
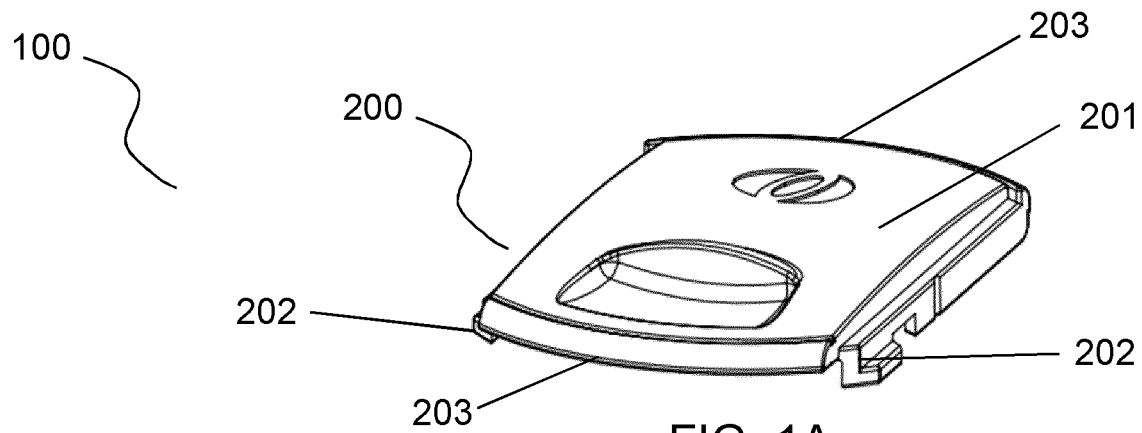
FIG. 1 shows an exploded view of an embodiment of lid for an ostomy implant comprising a slider (FIG. 1A), a cap part (FIG. 1B), and a ring-shaped base part (FIG. 1C)

All drawings are exemplary and not limiting to the presently disclosed lid and method of manufacturing the lid.

DETAILED DESCRIPTION

The present disclosure relates to a lid for an ostomy implant. The lid comprises three parts, which each may have improved features related to the operation of the lid.

The first part is a ring-shaped base part adapted to engage with an open end of the ostomy implant.

The second part is a cap part adapted to fit inside the ring-shaped base part, wherein the cap part is rotatable with respect to the ring-shaped base part to lock and unlock the lid to the ostomy implant, and wherein the cap part has a through-hole.

The third part is a slider configured to be radially slid into a recess of the cap part in a closed configuration, wherein the slider completely covers the through-hole of the cap part, and radially slid out from the recess in an open configuration, wherein the slider does not cover the through-hole of the cap part.

The cap part is rotatable with respect to the ring-shaped base part to lock and unlock the lid to the ostomy implant. Thus, rotation of the cap part relative to the ring-shaped base part (or vice versa) causes the lid to attach to the implant part. 'Rotation' of the cap part and ring-shaped base part shall be construed as a turning movement around a longitudinal axis of the ring-shaped base part and cap part. These parts may have generally cylindrical shapes. The rotation/turning can thus be seen as a rotation around a longitudinal axis of such generally cylindrical shapes. The cap part may thus be rotatable with respect to the ring-shaped base part into a locked configuration, wherein the lid cannot be removed from the ostomy implant, and into an unlocked configuration, wherein the lid can be removed from the ostomy implant.

FIGS. 15A-C show basic operation of the lid. In FIG. 15A the lid (100) is in a closed and locked position. In one embodiment, the cap part (300) is locked with respect to the ring-shaped base part (400) when the slider (200) is in the closed configuration. In FIG. 15B the slider (200) has been slid to a retracted position. This can be done without any turning. The position in FIG. 15B can be referred to as a locked and open configuration. This configuration can be used during a process in which waste leaves the stoma. From the position of FIG. 15B the cap part (300) and the ring-shaped base part (400) can be rotated relative to each other to the position of FIG. 15C, which shows the lid in an open and unlocked configuration, wherein the lid can be removed from the ostomy implant. Thus, in one embodiment of the presently disclosed lid (100), the cap part (300) is rotatable with respect to the ring-shaped base part (400) when the slider (200) is in the open configuration. Preferably, the slider (200) is rotatably locked to the cap part (300), which means that it can only be moved in a radial direction, i.e. between the closed position, wherein the slider (200) completely covers the through-hole (304) of the cap part (300), and the open configuration, in which the slider (200) does not cover at least a part of the through-hole (304) of the cap part (300). In the open configuration the slider (200) protrudes outwardly and can thus be used as a lever or handle for rotating the cap part (300) with respect to the ring-shaped base part (400). In one embodiment, the slider can, in the open configuration, be used to rotate the cap part with respect to the ring-shaped base part to lock and unlock the lid to the ostomy implant.

Figure 5:
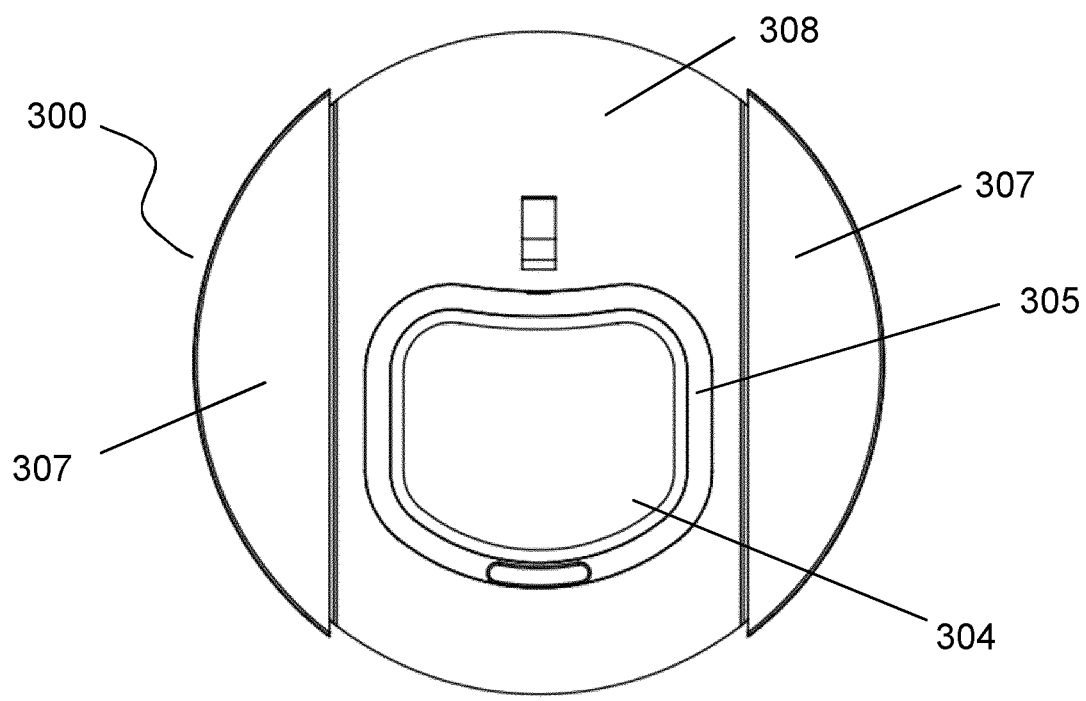
FIG. 5 shows an upper view of an embodiment of a cap part.

In one embodiment, the cap part further comprises an upper gasket around the through-hole as shown in the example in FIG. 5. The upper gasket (305) may be arranged in an upper cap groove, which is not visible in FIG. 5. The upper gasket may protrude upwardly into the recess of the cap part. In one embodiment the upper gasket protrudes less than 3 mm. Preferably, the slider and the upper gasket form a liquid-tight sealing in the closed configuration.

Figure 2:
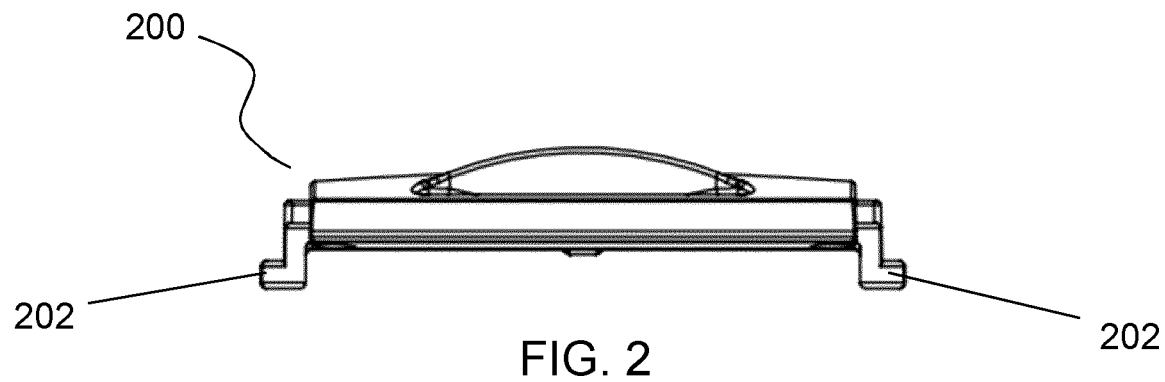
FIG. 2 shows an embodiment of a slider.
Figure 3:
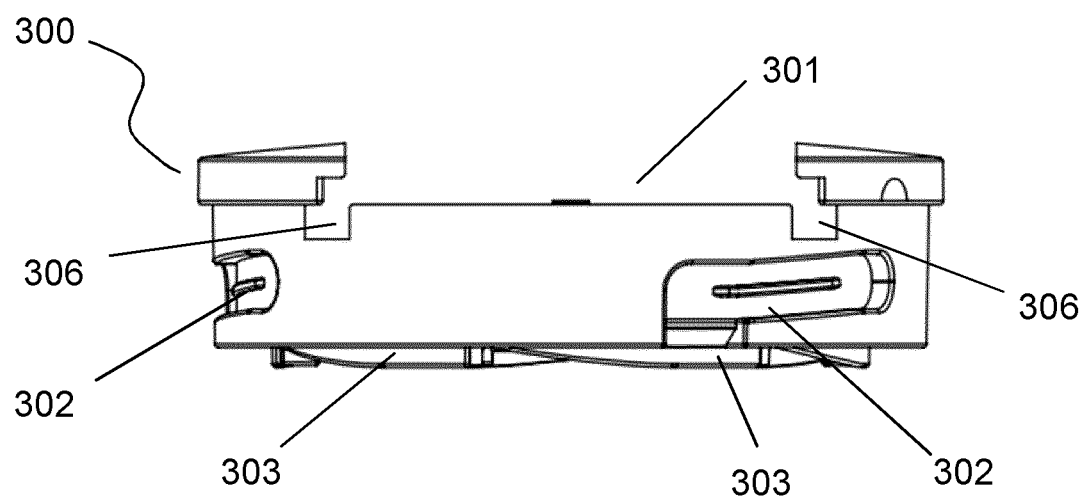
FIG. 3 shows a side view of an embodiment of a cap part.

In one embodiment the slider comprises two lower side guide rails. The cap part may comprise two corresponding guide grooves for guiding the two lower side guide rails. FIGS. 2 and 3 show an example of two lower side guide rails (202) and two corresponding guide grooves (306).

The slider may be dimensioned so as to extend across a diameter of the lid, when assembled. As such, the slider may be substantially rectangular but may have slightly curved ends to match the circumference of the lid. The slider may have a curved upper surface with the curvature of this surface extending along the length of the slider. The recess of the cap part may, accordingly, be dimensioned such that the slider can be slid through it.

Figure 10:
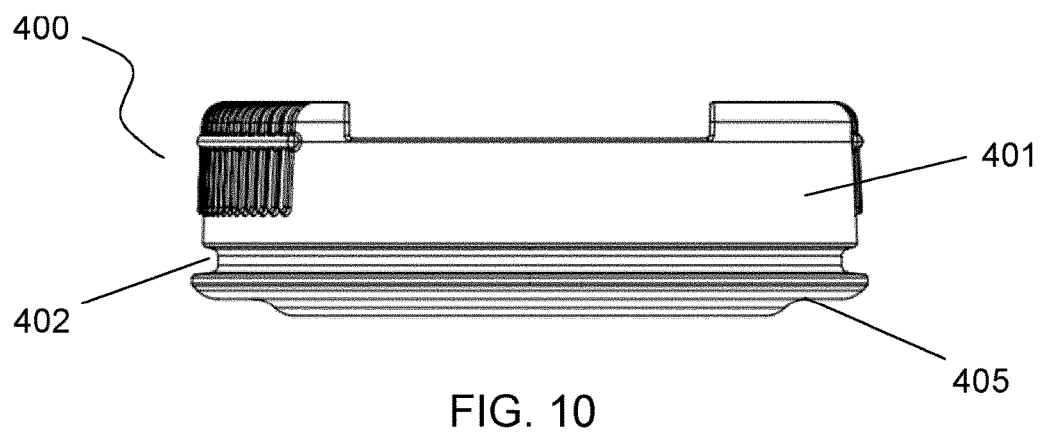
FIG. 10 shows a side view of an embodiment of a ring-shaped base part.

By controlling the locking of the ring-shaped base part to the ostomy implant by means of rotation of the cap part, a solution that is easy to use for the wearer is obtained. The ring-shaped base part may comprise a substantially cylindrical sidewall (401) and a substantially flat bottom ring part (405), as shown in the example of FIG. 10. The substantially flat bottom ring part may be a substantially flat annular structure. As would be understood by a person skilled in the art, the structure does not necessarily have to be completely flat.

The ring-shaped base part comprises a plurality of locking hooks. The locking hooks may be configured to engage with a circumferential groove of the ostomy implant. Examples of locking hooks (404) can be seen in FIG. 8. Moreover, in the example of FIG. 12, it can be seen how a locking hook (404) engages with a circumferential groove (501) of an ostomy implant (500). The locked configuration is represented by the locking hook (404) being in position 404b.

Preferably, the locking hooks are made of a flexible and/or resilient material. The material may be, for example, a plastic material. One advantage of having a resilient material is that the locking hooks then may have a default configuration in which they do not engage with the circumferential groove of the ostomy implant. If a mechanism is used for pushing and holding the locking hooks in the circumferential groove of the ostomy implant in the locked configuration, the locking hooks can automatically return to their default configurations when the mechanism for pushing and holding the locking hooks in the circumferential groove is deactivated or released.

The locking hooks may be arranged on an inner edge of the bottom ring part. The locking hooks may point upwardly and have a slightly inwardly bent edge. 'Upwardly' shall in this regard be construed as a longitudinal direction of the cylindrical base part towards the slider. 'Inwardly' refers to a radial direction of the cylindrical base part towards the center of the cylindrical base part. Thus, the locking hooks may be resilient pins with hooks configured to engage with a circumferential groove of the ostomy implant.

As would be recognized by a person skilled in the art, the implementation is not limited to a certain number of locking hooks. Any suitable number of locking hooks may be used.

Figure 12:
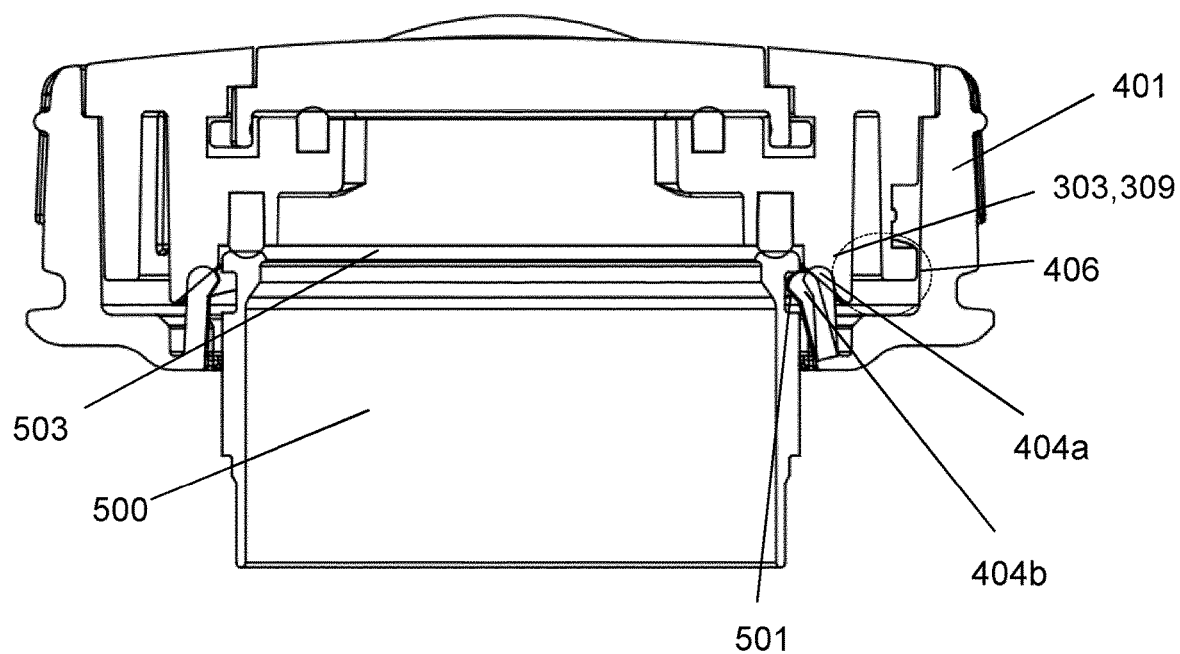
FIG. 12 shows a further cross-sectional side view of an embodiment of a ring-shaped base part engaging with a circumferential groove of the ostomy implant.
Figure 13:
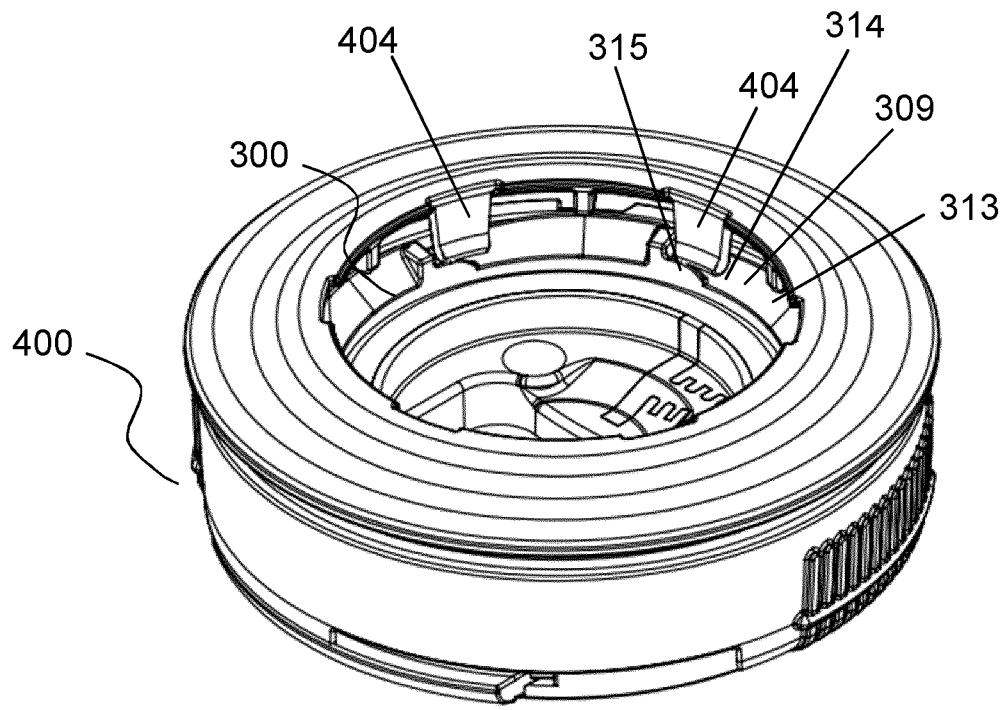
FIG. 13 shows embodiments of a ring-shaped base part and a cap part in an unlocked configuration.

As stated, the lid may further comprise a mechanism for holding the locking hooks in the circumferential groove of the ostomy implant in the locked configuration. Such a mechanism may be implemented by means of blocking elements on the cap part. Preferably, the blocking elements are distributed on the cap part to match the locking hooks. Therefore, in one embodiment, the cap part comprises a plurality of blocking elements corresponding to the plurality of locking hooks of the ring-shaped base part. In the example of FIG. 12, it can be seen how a locking hook (404) engages with a circumferential groove (501) of an ostomy implant (500) in position 404b. A blocking element (303) forces the locking hook (404) into the circumferential groove (501) of the ostomy implant (500). In the example, the blocking element (303) is arranged in a space (406) defined by the substantially cylindrical sidewall (401) and the locking hooks (404) of the ring-shaped base part (400). The plurality of blocking elements may be configured to block the plurality of locking hooks to move from the circumferential groove of the ostomy implant in the locked configuration. In the unlocked configuration, the locking hooks can move out from the circumferential groove of the ostomy implant in the unlocked configuration. This functionality can be obtained by having a blocking element with a curved shape extending along a sector of the cap part. Alternatively, the blocking element can be described as having a shape of a section of a spiral. When the cap part rotates with respect to the ring-shaped base part, i.e. also with respect to the locking hooks of the ring-shaped parts, a part of the blocking element that performs the blocking can be aligned with the locking hooks in the locked configuration. The blocking element can be arranged such that a distance of the blocking element with respect to a center of the cap gradually increases along the curved shape. When the cap part is rotated towards the locked configuration, the blocking element may therefore gradually force the locking hook towards the circumferential groove of the ostomy implant. Embodiments of blocking elements (309) can be seen in, for example, FIG. 6, FIG. 7 and FIG. 13. The blocking element may have a proximal section (313) and a distal section (314), as shown in, for example, FIG. 6. A proximal section of a curved shape may block one of the locking hooks in the locked configuration, whereas a distal section of the curved shape allows the locking hooks to move out from the circumferential groove of the ostomy implant in the unlocked configuration. The blocking elements can be implemented as chamfers (309), as shown in FIG. 7 and FIG. 13. Each chamfer may be a sloping edge. Provided that the blocking elements also may have a shape such that a distance of the blocking element with respect to a center of the cap gradually increases along the curved shape, the overall shape of the chamfer may, in one embodiment, be described as a shape of a section of a spiral with a slope. The slope may be oriented downwardly and inwardly in the cap part. A rotation of the cap part with respect to the ring-shaped base part may to lock the lid may control an alignment of the plurality of blocking elements and the plurality of locking hooks. As stated this can be done by holding and turning the slider which is rotatably locked to the cap part.

Each blocking element may further comprise a retraction element configured to guide and maintain the locking hooks away from the circumferential groove of the ostomy implant in the unlocked configuration. When the cap part is rotated with respect to the ring-shaped base part from the locked configuration to the unlocked configuration, the locking hooks may, at least to some extent, get stuck in the circumferential groove of the ostomy implant. The retraction element may assist in actively moving the locking hooks out of the circumferential groove when the cap part is turned to the unlocked configuration. FIG. 13 shows an embodiment of a blocking element (309) having a retraction element (315). In the figure, the locking hook (404) has been guided to a retracted position by the retraction element (315) of the blocking element (309). The lid is in an unlocked position. The retraction element (315) is located in the distal section (314) of the blocking element (309). The retraction element (315) in the example has the shape of a plate towards the center of the cap part with a sloping upper edge. The plate may have an angle with respect to the center of the cap part such that it can guide the locking hook (404) into the retracted position behind the retraction element (315) in the unlocked configuration.

The cap part may further comprise a lower gasket towards the ostomy implant. The lower gasket and an upper circumferential edge part of the ostomy implant may form a liquid-tight connection in the locked configuration.

The ring-shaped base part and the cap part may comprise complementary guide elements, which are used for the rotation of the ring-shaped base part and the cap part relative to each other. In one embodiment, the complementary guide elements comprise one or more grooves provided on the cap part, and one or more complementary protruding elements provided on the ring-shaped base part, wherein the one or more protruding elements are arranged to extend into the one or more grooves, thereby allowing the cap part and the ring-shaped base part to rotate relative to each other. The cap part and the ring-shaped base part may be arranged such that as the cap part is rotated relative to the ring-shaped base part, the cap part is also made to move axially with respect to the ring-shaped base part. Such an axial movement caused by rotation of the cap part relative to the ring-shaped part may cause a lower gasket facing an upper circumferential edge part of the ostomy implant to be pushed against the upper circumferential edge part of the ostomy implant.

The ring-shaped base part may further comprise an outer circumferential groove.

The present disclosure further relates to an ostomy implant assembly having a circumferential groove and a lid according to any one of the preceding claims.

The present disclosure further relates to a method of manufacturing the presently disclosed lid, the method comprising the steps of:
- providing a ring-shaped base part adapted to engage with an open end of the ostomy implant;
- providing a cap part adapted to fit inside the ring-shaped base part, wherein the cap part is rotatable with respect to the ring-shaped base part to lock and unlock the lid to the ostomy implant, and wherein the cap part has a through-hole;
- providing a slider configured to be radially slid into a recess of the cap part in a closed configuration, wherein the slider completely covers the through-hole of the cap part, and radially slid out from the recess in an open configuration, wherein the slider does not cover the through-hole of the cap part; and
- assembling the ring-shaped base part, the cap part and the slider.

As would be understood by a person skilled in the art, the method of manufacturing the presently disclosed lid may, in particular, be used to assemble a lid as described in the present disclosure. The ring-shaped base part, cap part and slider may be of any suitable material, for example, plastic materials, such as polyethylene, polypropylene, polycarbonate (PC) or polymethylmethacrylate (PMMA). However, others may also be used. The main part of the ring-shaped base part, cap part and slider may thereby be molded. In the event that additional components are used, they can be mounted on the molded ring-shaped base part, cap part and slider.

DETAILED DESCRIPTION OF THE DRAWINGS

The invention will in the following be described in greater detail with reference to the accompanying drawings. The drawings are examples of embodiments and are intended to illustrate some of the features of the presently disclosed lid, and are not to be construed as limiting to the presently disclosed invention.

Figure 1B:
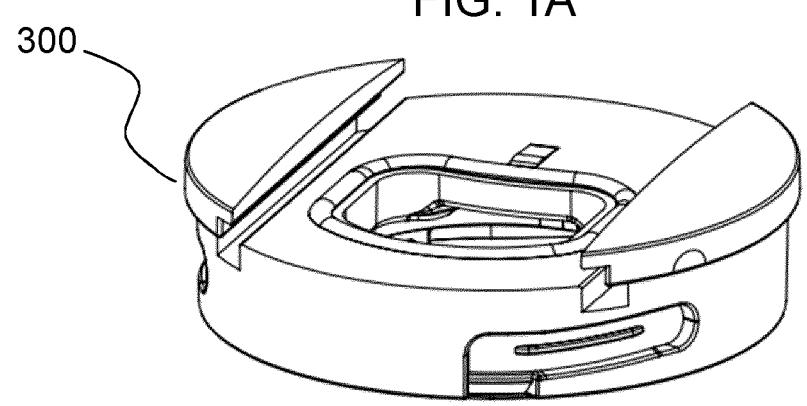
Figure 1C:
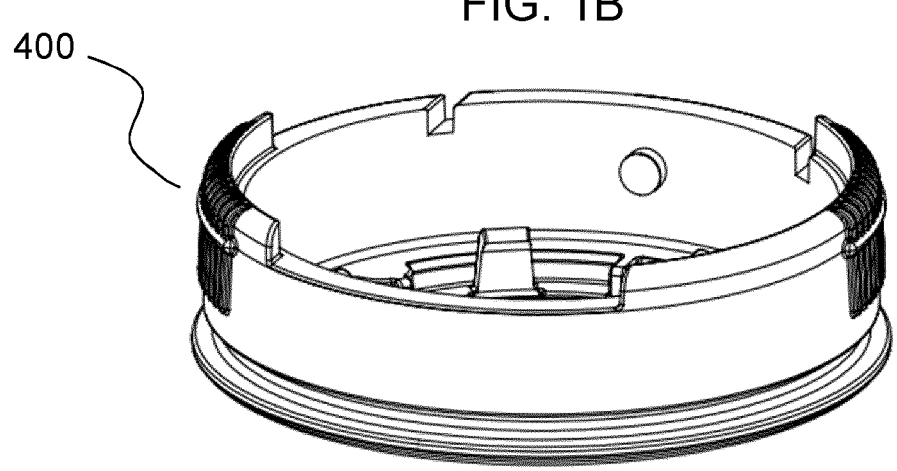

FIG. 1 shows an exploded view of an embodiment of lid (100) for an ostomy implant comprising a slider (200), a cap part (300), and a ring-shaped base part (400). The slider (200) has a slightly curved upper surface (201), lower side guide rails (202) and curved ends (203) that match the circumference of the rest of the lid (100), in particular the cap part (300).

FIG. 2 shows a cross-sectional view of an embodiment of a slider (200). The slider has two lower side guide rails (202).

FIG. 3 shows a side view of an embodiment of a cap part (300). The cap part (300) has a recess (301) that the slider (200) can be slid into. In particular, the two lower side guide rails (202) of the slider (200) can be slid into the corresponding guide grooves (306) of the cap part (300). The cap part (300) further comprises grooves (302) provided on a sidewall of the cap part (300). The grooves (200) are oriented in a mainly horizontal direction but also extend in the vertical/axial direction of the cap part (300), so as to create an axial movement of the cap part (300) relative to a base part (400) when the cap part (300) and the ring-shaped base part (400) are rotated in relation to each other.

Figure 4:
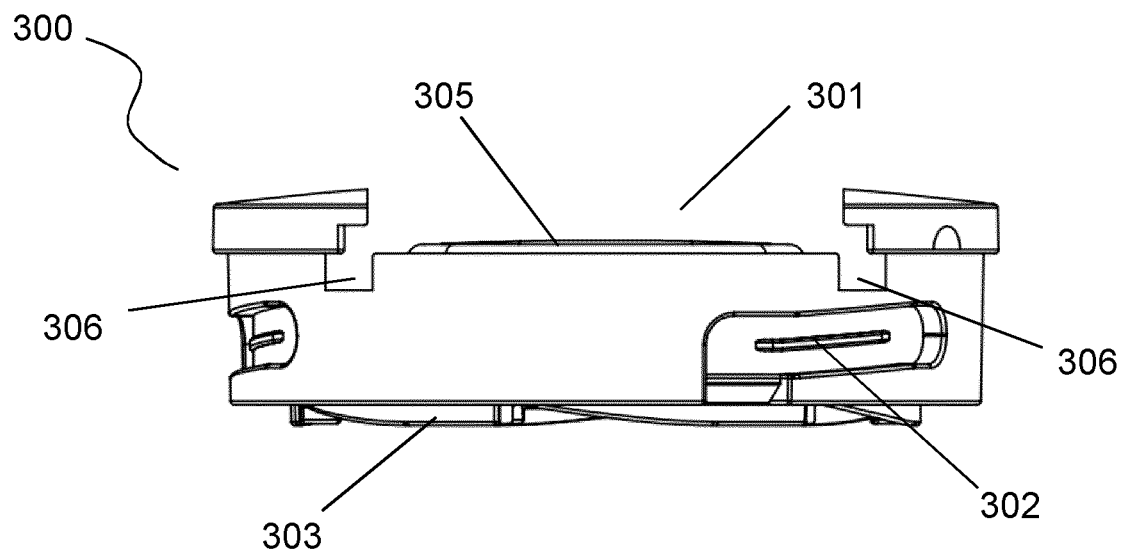
FIG. 4 shows a further side view of an embodiment of a cap part.

FIG. 4 shows a further side view of an embodiment of a cap part (300). The cap part (300) has a recess (301) that the slider (200) can be slid into. In particular, the two lower side guide rails (202) of the slider (200) can be slid into the corresponding guide grooves (306) of the cap part (300). The cap part (300) further comprises grooves (302) provided on a sidewall of the cap part (300). The cap part (300) further comprises an upper gasket (305) around the through-hole. The upper gasket (305) protrudes slightly upwardly into the recess (301) of the cap part (300).

FIG. 5 shows an upper view of an embodiment of a cap part (300). From the upper view a recess upper surface (308) and a cap upper surface (307) can be seen. In the recess (301), on the recess upper surface (308), there is a through-hole (304). The cap part (300) further comprises an upper gasket (305) arranged around the through-hole (304). The upper gasket (305) is arranged in an upper cap groove (not visible).

Figure 6:
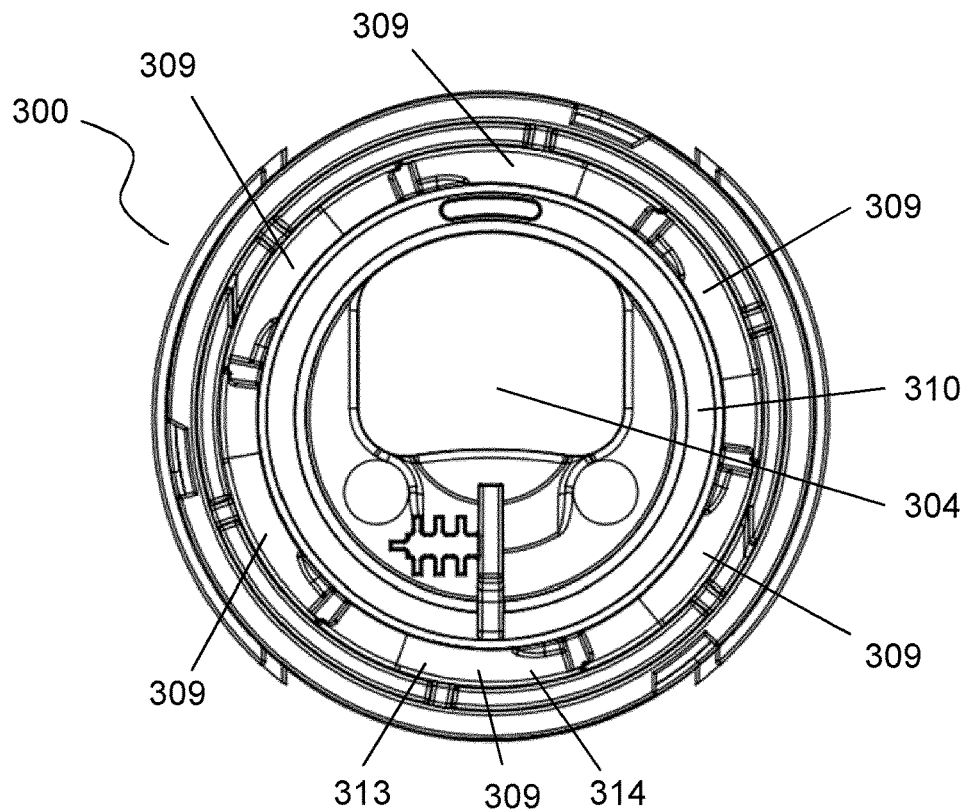
FIG. 6 shows a lower view of an embodiment of a cap part.
Figure 7:
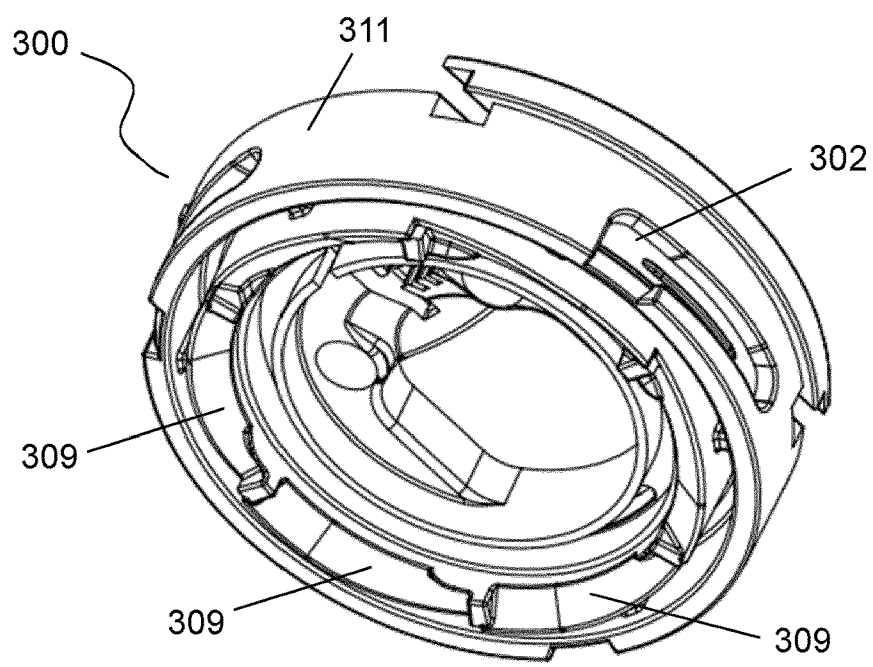
FIG. 7 shows a perspective view of an embodiment of a cap part.

FIG. 6 shows a lower view of an embodiment of a cap part (300). The cap part has six blocking elements (309) designed as chamfers (309) evenly distributed on an inner edge, around the through-hole (304) of the cap part (300). Each blocking element (309) has a proximal section (313) and a distal section (314). A lower gasket (310) is also visible.

FIG. 7 shows a lower perspective view of an embodiment of a cap part (300). The cap part (300) comprises grooves (302) provided on a cap sidewall (311) of the cap part (300). Blocking elements (309) can also be seen from the underside of the cap part (300).

Figure 8:
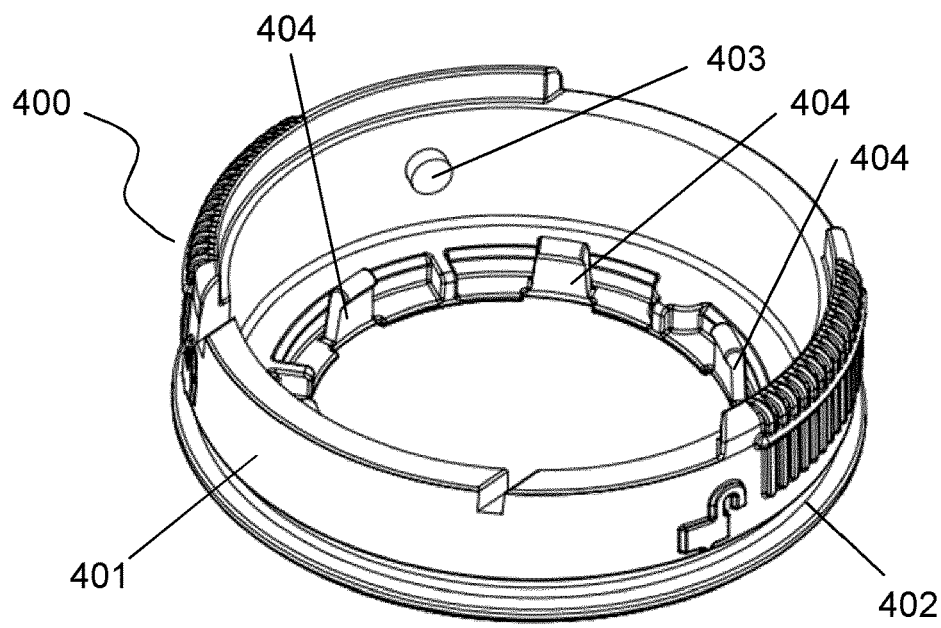
FIG. 8 shows a perspective view of an embodiment of a ring-shaped base part.

FIG. 8 shows a perspective view of an embodiment of a ring-shaped base part (400). The ring-shaped base part (400) comprises protruding elements (403) provided on the inside of a sidewall (401) of the ring-shaped base part (400). The ring-shaped base part (400) comprises a number of locking hooks (404) and an outer circumferential groove (402).

Figure 9:
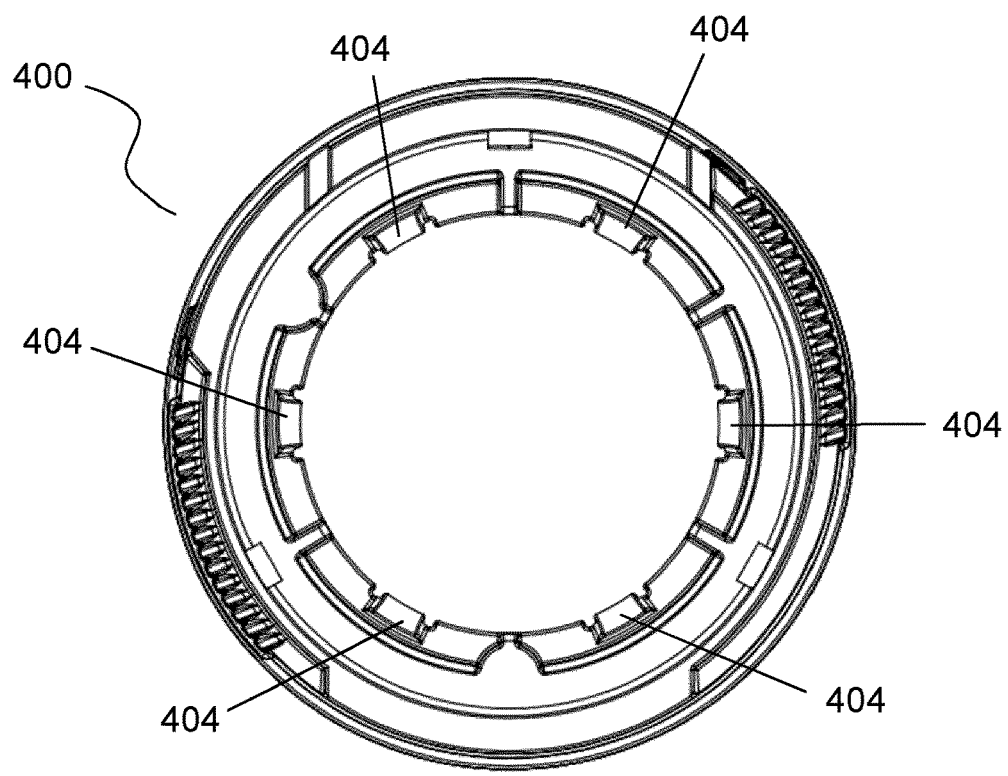
FIG. 9 shows an upper view of an embodiment of a ring-shaped base part.

FIG. 9 shows an upper view of an embodiment of a ring-shaped base part (400). The ring-shaped base part (400) comprises six locking hooks (404) evenly distributed on the inside of the ring-shaped base part (400).

FIG. 10 shows a side view of an embodiment of a ring-shaped base part (400) having a cylindrical sidewall (401), an outer circumferential groove (402), and a bottom ring part (405).

Figure 11:
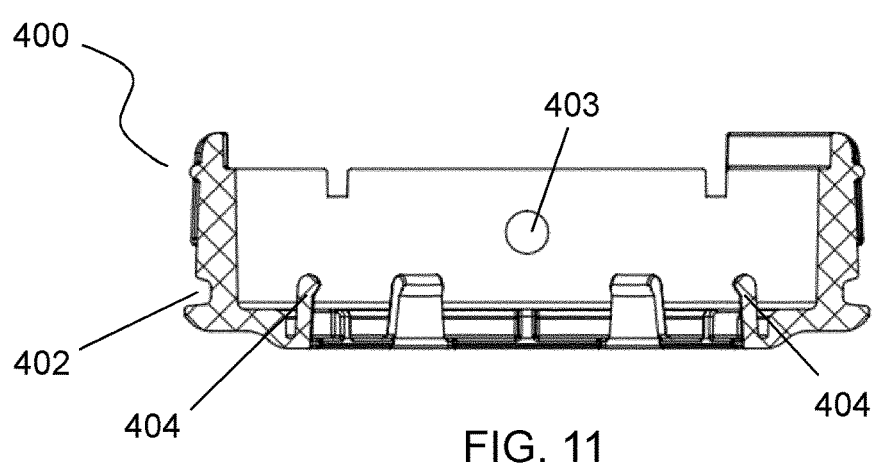
FIG. 11 shows a cross-sectional side view of an embodiment of a ring-shaped base part.

FIG. 11 shows a cross-sectional side view of an embodiment of a ring-shaped base part (400). The ring-shaped base part (400) has a protruding element (403) and an outer circumferential groove (402). The ring-shaped base part (400) also shows two locking hooks (404).

FIG. 12 shows a further cross-sectional side view of an embodiment of a ring-shaped base part (400) engaging with a circumferential groove (501) of an ostomy implant (500). The ostomy implant (500) has an upper circumferential edge part (503). A locking hook (404) engages with the circumferential groove (501) of the ostomy implant (500) in position 404b. A blocking element (303) forces the locking hook (404) into the circumferential groove (501) of the ostomy implant (500). In the example, the blocking element (303) is arranged in a space (406) defined by the substantially cylindrical sidewall (401) and the locking hooks (404) of the ring-shaped base part (400). FIG. 13 shows embodiments of a ring-shaped base part (400) and a cap part (300) in an unlocked configuration. One of the blocking elements (309) has a proximal section (313) and a distal section (314). The proximal section (313) may be adapted to maintain the locking hook (404) of the base part (400) in the circumferential groove of the ostomy implant in a locked configuration. FIG. 13, however, shows an unlocked configuration, in which the distal section (314) is aligned with the locking hook (404). In the example the blocking element (309) further comprises a retraction element (315). The retraction element (315) in the example has the shape of a plate towards the center of the cap part with a sloping upper edge. The plate may have an angle with respect to the center of the cap part such that it can guide the locking hook (404) into the retracted position behind the retraction element (315) in the unlocked configuration.

Figure 14:
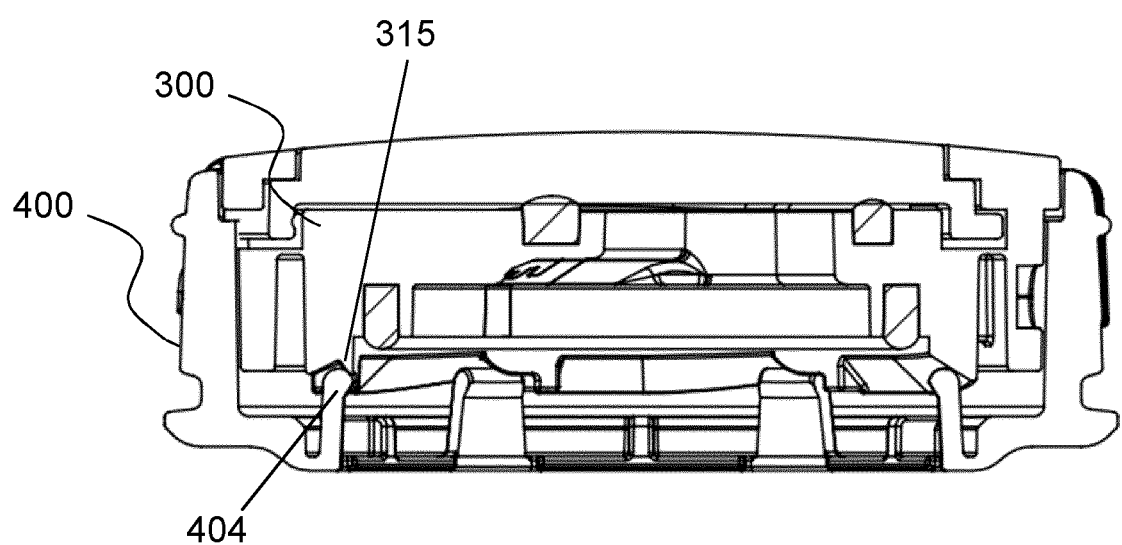
FIG. 14 shows embodiments of a ring-shaped base part and a cap part in an unlocked configuration.

FIG. 14 shows embodiments of a ring-shaped base part (400) and a cap part (300) in an unlocked configuration. In this configuration it can be seen how the retraction element (315) asserts an outward force on the locking hook (404) to guide it away from the circumferential groove of the ostomy implant.

FIG. 15 shows configurations of opening/closing and locking of the lid (100). In FIG. 15A the lid (100) is a closed and locked position. The cap part (300) is locked with respect to the ring-shaped base part (400) when the slider (200) is in the closed configuration. In FIG. 15B the slider (200) has been slid to a retracted position. This can be done without any turning. The position in FIG. 15B can be referred to as a locked and open configuration. From the position of FIG. 15B the cap part (300) and the ring-shaped base part (400) can be rotated relative to each other to the position of FIG. 15C, which shows the lid (100) in an open and unlocked configuration, wherein the lid can be removed from the ostomy implant. In the open configuration the slider (200) protrudes outwardly and can thus be used as a lever or handle for rotating the cap part (300) with respect to the ring-shaped base part (400).

Figure 16:
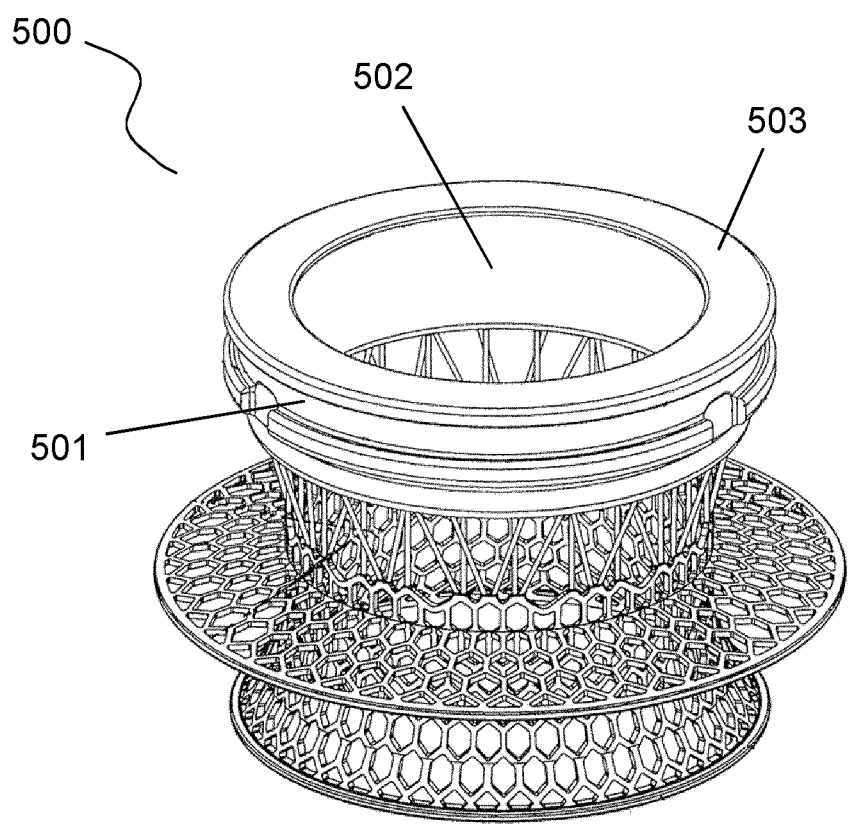
FIG. 16 shows an example of an ostomy implant.

FIG. 16 shows an example of a percutaneous ostomy implant (500). The ostomy implant comprises a tubular interior section, formed mainly of mesh, and a circular, radially-extending anchoring flange or dermal anchor. The ostomy implant (500) has a circumferential groove (501), an open end (502) and an upper circumferential edge part (503).

Figure 17:
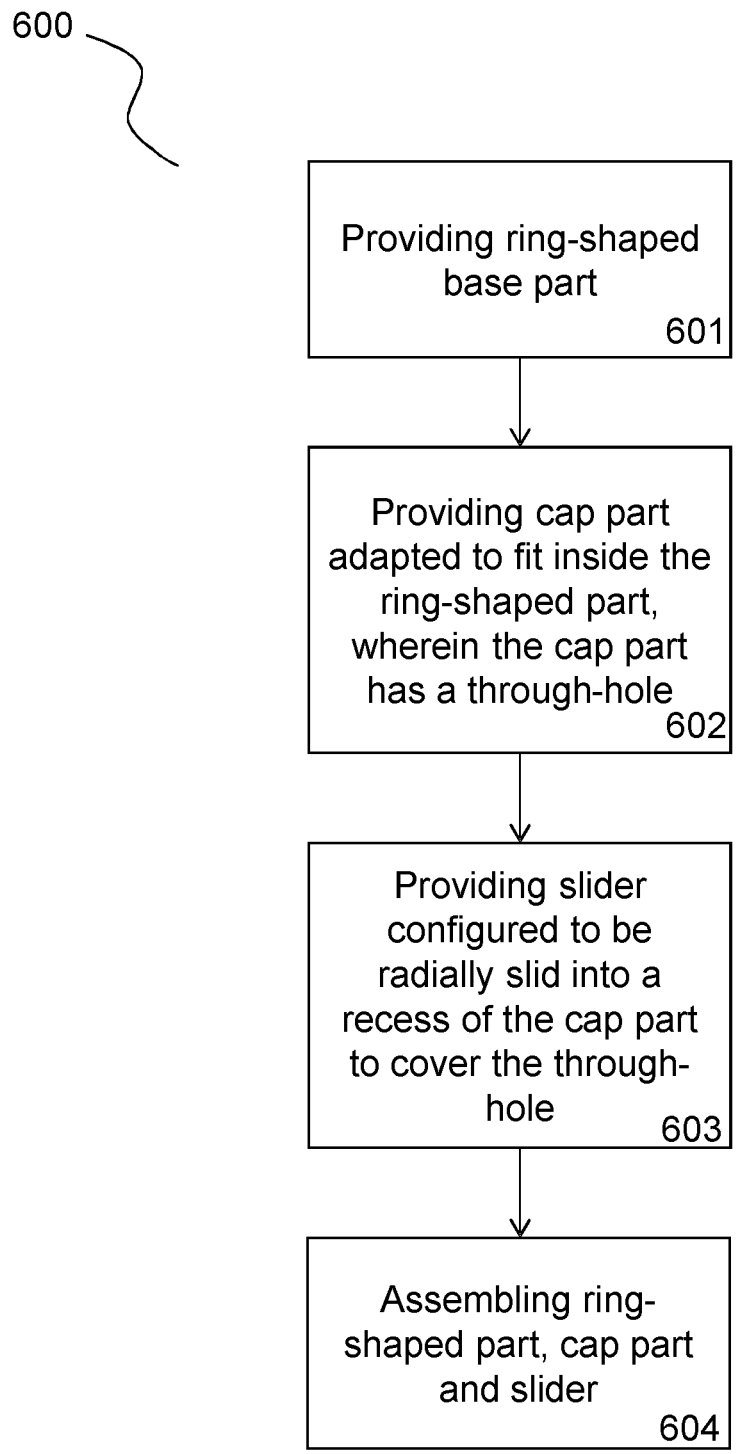
FIG. 17 shows an embodiment of the method of manufacturing the presently disclosed lid.

FIG. 17 shows an embodiment of a method (600) of manufacturing the presently disclosed lid. The method (600) comprises the steps of:
  providing a ring-shaped base part adapted to engage with an open end of the ostomy implant (601);
  providing a cap part adapted to fit inside the ring-shaped base part, wherein the cap part is rotatable with respect to the ring-shaped base part to lock and unlock the lid to the ostomy implant, and wherein the cap part has a through-hole (602);
  providing a slider configured to be radially slid into a recess of the cap part in a closed configuration, wherein the slider completely covers the through-hole of the cap part, and radially slid out from the recess in an open configuration, wherein the slider does not cover the through-hole of the cap part (603); and
  assembling the ring-shaped base part, the cap part and the slider (604).

LIST OF ELEMENTS IN FIGURES

100—lid
200—slider
201—curved upper surface
202—lower side guide rails
203—curved end
300—cap part
301—recess
302—groove
303—blocking element
304—through-hole
305—upper gasket
306—guide grooves
307—cap upper surface
308—recess upper surface
309—chamfer
310—lower gasket
311—cap sidewall
313—proximal section
314—distal section
315—retraction element
400—ring-shaped base part
401—sidewall
402—outer circumferential groove
403—protruding element
404—locking hook
405—bottom ring part
406—space defined by cylindrical sidewall and locking hooks
500—ostomy implant
501—circumferential groove
502—open end
503—upper circumferential edge part

FURTHER DETAILS

1. A lid for an ostomy implant, comprising:
  a ring-shaped base part adapted to engage with an open end of the ostomy implant;
  a cap part adapted to fit inside the ring-shaped base part, wherein the cap part is rotatable with respect to the ring-shaped base part to lock and unlock the lid to the ostomy implant, and wherein the cap part has a through-hole; and
  a slider configured to be radially slid into a recess of the cap part in a closed configuration, wherein the slider completely covers the through-hole of the cap part, and radially slid out from the recess in an open configuration, wherein the slider does not cover the through-hole of the cap part.

2. The lid according to item 1, wherein the cap part is rotatable with respect to the ring-shaped base part when the slider is in the open configuration.

3. The lid according to any one of the preceding items, wherein the cap part is locked with respect to the ring-shaped base part when the slider is in the closed configuration.

4. The lid according to any one of the preceding items, wherein the cap part further comprises an upper gasket around the through-hole.

5. The lid according to item 4, wherein the upper gasket is arranged in an upper cap groove.

6. The lid according to any one of items 4-5, wherein the upper gasket protrudes upwardly into the recess of the cap part.

7. The lid according to item 6, wherein the upper gasket protrudes less than 3 mm.

8. The lid according to any one of items 4-7, wherein the slider and the upper gasket form a liquid-tight sealing in the closed configuration.

9. The lid according to any one of the preceding items, wherein the ring-shaped base part comprises a substantially cylindrical sidewall and a substantially flat bottom ring part.

10. The lid according to any one of the preceding items, wherein the ring-shaped base part comprises a plurality of locking hooks.

11. The lid according to item 10, wherein the plurality of locking hooks are configured to engage with a circumferential groove of the ostomy implant.

12. The lid according to any one of items 10-11, wherein the locking hooks are made of a flexible and/or resilient material.

13. The lid according to item 9 and any one of items 10-12, wherein the locking hooks are arranged on an inner edge of the bottom ring part.

14. The lid according to item 9 and any one of items 10-13, wherein the locking hooks are resilient pins with hooks configured to engage with a circumferential groove of the ostomy implant.

15. The lid according to any one of items 10-14, wherein the cap part comprises a plurality of blocking elements corresponding to the plurality of locking hooks of the ring-shaped base part.

16. The lid according to item 15, wherein the plurality of blocking elements are arranged in a space defined by the substantially cylindrical sidewall and the locking hooks of the ring-shaped base part.

17. The lid according to any one of the preceding items, wherein the cap part is rotatable with respect to the ring-shaped base part into a locked configuration, wherein the lid cannot be removed from the ostomy implant, and into an unlocked configuration, wherein the lid can be removed from the ostomy implant.

18. The lid according to any one of items 15-16 and item 17, wherein the plurality of blocking elements are configured to block the plurality of locking hooks to move from the circumferential groove of the ostomy implant in the locked configuration.

19. The lid according to any of items 15-18, wherein the locking hooks can move out from the circumferential groove of the ostomy implant in the unlocked configuration.

20. The lid according to any of items 15-19, wherein each blocking element has a curved shape extending along a sector of the cap part.

21. The lid according to item 20, wherein each blocking element is arranged such that a distance of the blocking element with respect to a center of the cap gradually increases along the curved shape.

22. The lid according to any of items 20-21, wherein a proximal section of the curved shape blocks one of the locking hooks in the locked configuration, and wherein a distal section of the curved shape allows the locking hooks to move from the circumferential groove of the ostomy implant in the unlocked configuration.

23. The lid according to any of items 15-22, wherein the blocking elements are chamfers.

24. The lid according to any of items 15-23, wherein each blocking element further comprises a retraction element configured to guide and maintain the locking hooks away from the circumferential groove of the ostomy implant in the unlocked configuration.

25. The lid according to any one of the preceding items, wherein the cap part further comprises a lower gasket towards the ostomy implant.

26. The lid according to item 25, wherein the lower gasket and an upper circumferential edge part of the ostomy implant form a liquid-tight connection in a locked configuration, wherein the lid cannot be removed from the ostomy implant.

27. The lid according to any one of the preceding items, wherein the slider, in the open configuration, can be used to rotate the cap part with respect to the ring-shaped base part to lock and unlock the lid to the ostomy implant.

28. The lid according to item 27, wherein a rotation of the cap part with respect to the ring-shaped base part to lock the lid controls an alignment of the plurality of blocking elements and the plurality of locking hooks.

29. The lid according to any one of the preceding items, wherein the ring-shaped base part and the cap part comprise complementary guide elements.

30. The lid according to item 29, wherein the complementary guide elements comprise one or more grooves provided on the cap part, and one or more complementary protruding elements provided on the ring-shaped base part, wherein the one or more protruding elements are arranged to extend into the one or more grooves, thereby allowing the cap part and the ring-shaped base part to rotate relative to each other.

31. The lid according to any one of items 29-30, wherein the cap part and the ring-shaped base part are arranged such that as the cap part is rotated relative to the ring-shaped base part, the cap part is also made to move axially with respect to the ring-shaped base part.

32. The lid according to item 31, wherein an axial movement caused by rotation of the cap part relative to the ring-shaped part causes a lower gasket facing an upper circumferential edge part of the ostomy implant to be pushed against the upper circumferential edge part of the ostomy implant.

33. The lid according to any one of the preceding items, wherein the slider comprises two lower side guide rails.

34. The lid according to item 33, wherein the cap part comprises two guide grooves for guiding the two lower side guide rails.

35. The lid according to any one of the preceding items, wherein the ring-shaped base part comprises an outer circumferential groove.

36. An implant assembly comprising an ostomy implant and a lid according to any one of the preceding items.

37. A method of manufacturing a lid according to any one of items 1-34, the method comprising the steps of:
 providing a ring-shaped base part adapted to engage with an open end of the ostomy implant;
 providing a cap part adapted to fit inside the ring-shaped base part, wherein the cap part is rotatable with respect to the ring-shaped base part to lock and unlock the lid to the ostomy implant, and wherein the cap part has a through-hole;
 providing a slider configured to be radially slid into a recess of the cap part in a closed configuration, wherein the slider completely covers the through-hole of the cap part, and radially slid out from the recess in an open configuration, wherein the slider does not cover the through-hole of the cap part; and assembling the ring-shaped base part, the cap part and the slider.

The invention claimed is:

1. A lid for an ostomy implant, comprising:
   a ring-shaped base part adapted to engage with an open end of the ostomy implant;
   a cap part adapted to fit inside the ring-shaped base part, wherein the cap part is rotatable with respect to the ring-shaped base part to lock and unlock the lid to the ostomy implant, and wherein the cap part has a through-hole; and
   a slider configured to be radially slid into a recess of the cap part in a closed configuration, wherein the slider completely covers the through-hole of the cap part, and radially slid out from the recess in an open configuration, wherein the slider does not cover the through-hole of the cap part.

2. The lid according to claim 1, wherein the cap part is rotatable with respect to the ring-shaped base part when the slider is in the open configuration, and wherein the cap part is locked with respect to the ring-shaped base part when the slider is in the closed configuration.

3. The lid according to claim 1, wherein the cap part further comprises an upper gasket around the through-hole, wherein the upper gasket is arranged in an upper cap groove.

4. The lid according to claim 3, wherein the upper gasket protrudes upwardly into the recess of the cap part, and wherein the slider and the upper gasket form a liquid-tight sealing in the closed configuration.

5. The lid according to claim 1, wherein the ring-shaped base part comprises a plurality of locking hooks, wherein the plurality of locking hooks are configured to engage with a circumferential groove of the ostomy implant.

6. The lid according to claim 5, wherein the locking hooks are made of a flexible or resilient material.

7. The lid according to claim 5, wherein the locking hooks are arranged on an inner edge of a substantially flat bottom ring part of the ring-shaped base part.

8. The lid according to claim 5, wherein the locking hooks are resilient pins with hooks configured to engage with a circumferential groove of the ostomy implant.

9. The lid according to claim 5, wherein the cap part comprises a plurality of blocking elements corresponding to the plurality of locking hooks of the ring-shaped base part.

10. The lid according to claim 9, wherein the cap part is rotatable with respect to the ring-shaped base part into a locked configuration, wherein the lid cannot be removed from the ostomy implant, and into an unlocked configuration, wherein the lid can be removed from the ostomy implant, wherein the plurality of blocking elements are configured to block the plurality of locking hooks to move from the circumferential groove of the ostomy implant in the locked configuration.

11. The lid according to claim 9, wherein each blocking element has a curved shape extending along a sector of the cap part, and wherein each blocking element is arranged such that a distance of the blocking element with respect to a center of the cap gradually increases along the curved shape.

12. The lid according to claim 11, wherein a proximal section of the curved shape blocks one of the locking hooks in the locked configuration, and wherein a distal section of the curved shape allows the locking hooks to move from the circumferential groove of the ostomy implant in the unlocked configuration.

13. The lid according to claim 9, wherein the blocking elements are chamfers.

14. The lid according to claim 9, wherein each blocking element further comprises a retraction element configured to guide and maintain the locking hooks away from the circumferential groove of the ostomy implant in the unlocked configuration.

15. The lid according to claim 1, wherein the cap part further comprises a lower gasket towards the ostomy implant.

16. The lid according to claim 1, wherein the slider, in the open configuration, can be used to rotate the cap part with respect to the ring-shaped base part to lock and unlock the lid to the ostomy implant.

17. The lid according to claim 1, wherein the ring-shaped base part and the cap part comprise complementary guide elements.

18. The lid according to claim 1, wherein the slider comprises two lower side guide rails.

19. An implant assembly comprising an ostomy implant and a lid according to claim 1.

20. A method of manufacturing a lid for an ostomy implant, the method comprising the steps of:
    providing a ring-shaped base part adapted to engage with an open end of the ostomy implant;
    providing a cap part adapted to fit inside the ring-shaped base part, wherein the cap part is rotatable with respect to the ring-shaped base part to lock and unlock the lid to the ostomy implant, and wherein the cap part has a through-hole;
    providing a slider configured to be radially slid into a recess of the cap part in a closed configuration, wherein the slider completely covers the through-hole of the cap part, and radially slid out from the recess in an open configuration, wherein the slider does not cover the through-hole of the cap part; and
    assembling the ring-shaped base part, the cap part and the slider.

* * * * *